United States Patent
Sonander

[19]

[11] Patent Number: 6,022,138

[45] Date of Patent: Feb. 8, 2000

[54] METHOD AND APPARATUS FOR MEASURING DEW POINT TEMPERATURE OF A MOIST GAS

[76] Inventor: Sven Olof Sonander, Puebla Blanca 17, Torreblanca del sol, 29640 Fuengirola, Malaga, Spain

[21] Appl. No.: 08/973,457

[22] PCT Filed: May 31, 1996

[86] PCT No.: PCT/GB96/01283

§ 371 Date: Dec. 2, 1997

§ 102(e) Date: Dec. 2, 1997

[87] PCT Pub. No.: WO96/38723

PCT Pub. Date: Dec. 5, 1996

[30] Foreign Application Priority Data

Jun. 2, 1995 [GB] United Kingdom .................. 9511204

[51] Int. Cl.[7] .................................................. G01N 25/68
[52] U.S. Cl. ............................................................ 374/28
[58] Field of Search ................................ 374/28, 18, 19

[56] References Cited

U.S. PATENT DOCUMENTS

| | | | |
|---|---|---|---|
| 2,106,593 | 1/1938 | Deniston et al. | 374/28 |
| 3,177,716 | 4/1965 | Warman | 374/18 |
| 3,937,059 | 2/1976 | Nisolle | 73/17 A |
| 5,165,793 | 11/1992 | Rall et al. | 374/28 |
| 5,364,185 | 11/1994 | VanZandt et al. | 374/28 |

FOREIGN PATENT DOCUMENTS

| | | |
|---|---|---|
| 0 202 453 | 11/1986 | European Pat. Off. . |
| 0 542 582 | 5/1993 | European Pat. Off. . |
| 2 316 587 | 1/1977 | France . |
| 2634274 | 2/1978 | Germany ........................... 374/28 |
| 2 043 908 | 10/1980 | United Kingdom . |
| 92 01926 | 2/1992 | WIPO . |
| 94 14055 | 6/1994 | WIPO . |

*Primary Examiner*—Diego Gutierrez
*Assistant Examiner*—Gail Verbitsky
*Attorney, Agent, or Firm*—Lahive & Cockfield, LLP

[57] ABSTRACT

A method for measuring the dew point temperature of a moist gas in which a flow of moist gas (A) is passed over a surface (2); a moisture sensor (5) is positioned in the flow of gas downstream of the surface (2); cooling is applied to the surface; the moisture content (M) of the gas downstream of the surface (2) is monitored; and the temperature of the surface (2) is measured, the temperature which is measured being controlled by the detection of a decrease in moisture content due to moisture condensation from the moist gas at the dew point temperature ($T_D$). An apparatus for carrying out the method is also described. The surface (2) may be a layer of heat-conducting material in contact with a heat pump (3) or the surface may be part of the wall of a coiled tube (40).

36 Claims, 6 Drawing Sheets

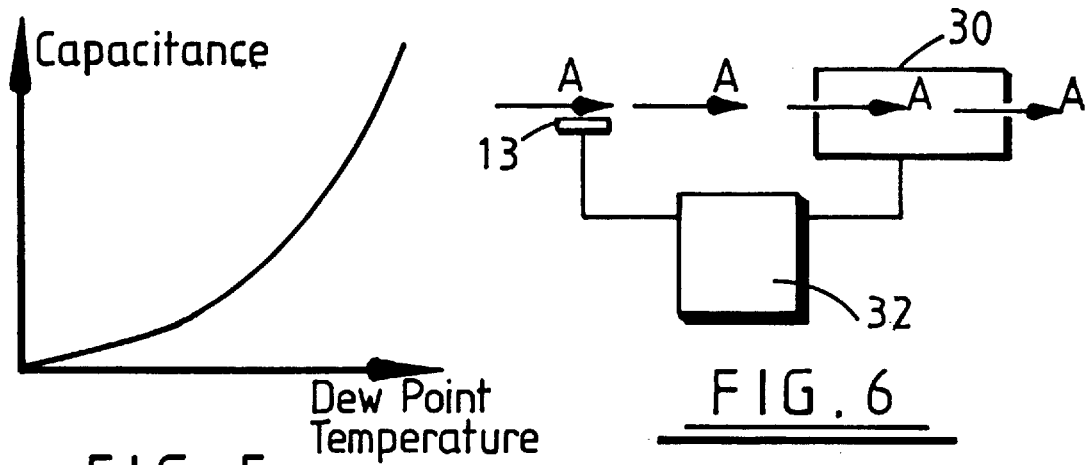
FIG. 5
FIG. 6
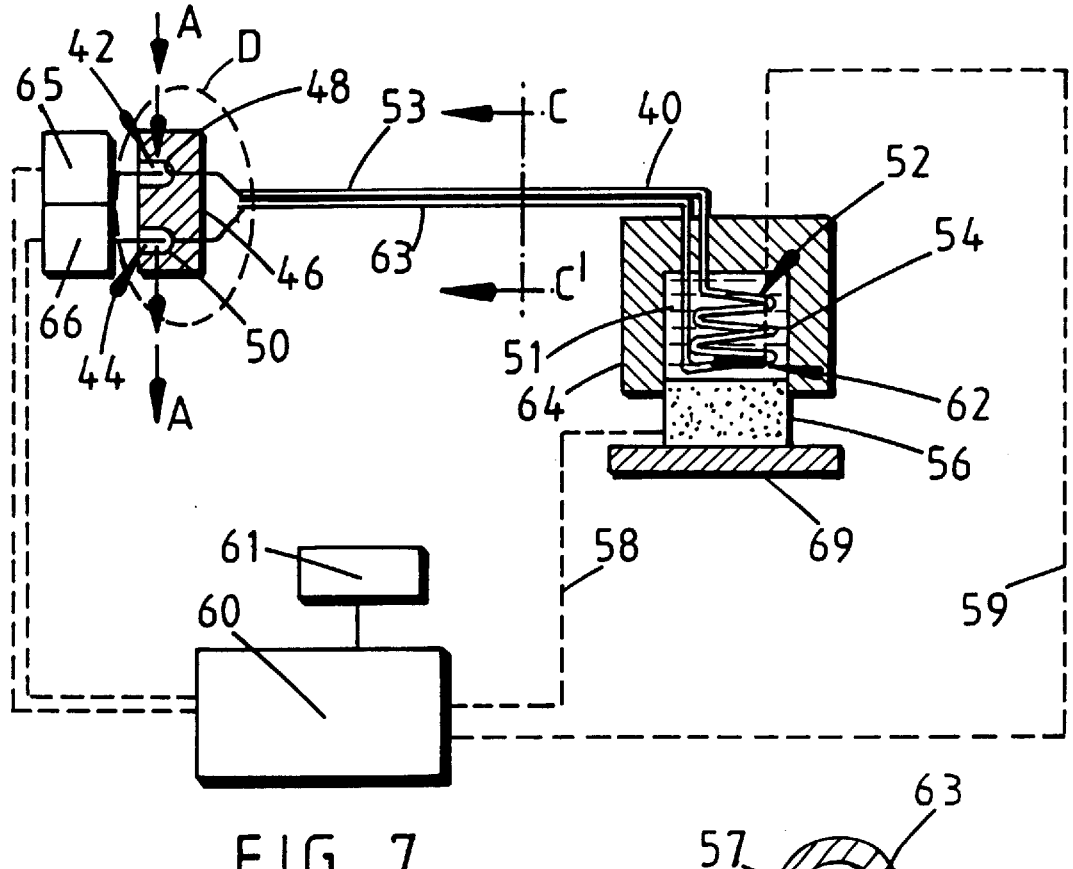
FIG. 7
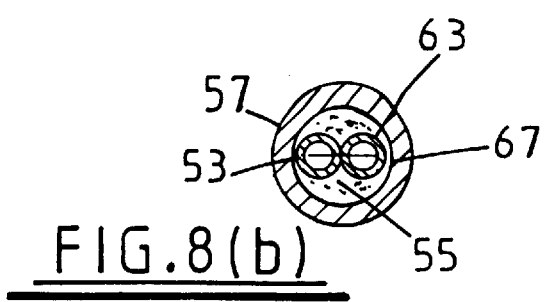
FIG. 8(b)

METHOD AND APPARATUS FOR MEASURING DEW POINT TEMPERATURE OF A MOIST GAS

BACKGROUND OF THE INVENTION

This invention relates to methods of measuring the dew point temperature of a moist gas, and apparatus suitable for carrying out such measurements.

The temperature at which a sample of a moist gas will become saturated and condense to form water droplets or, alternatively, frost, on a surface with which the moist gas is in contact is known as the "dew point" temperature. Generally, where the dew point temperature is above 0° the moist gas condenses to form water droplets at the dew point temperature, and where the dew point temperature is below 0° C. moist gas condenses to form frost. Although dew points below 0° C. are sometimes referred to as frost points, in the present context the term "dew point temperature" is intended to include dew point temperatures both above and below 0°.

It is often important to measure the dew point temperature of a moist gas, for example, one constituting the atmosphere inside a furnace such as a metallurgical furnace used in semiconductor or fabrication processes. The dew point temperature can provide a measure of the water content in the gas which must be kept extremely low in order to protect one or more of the product, a catalyst, and equipment used in the production process against damage e.g. in optical fibre manufacture. Dew point temperature measurements are also important in protecting gas pipelines against corrosion from moisture in the gas supply. Additionally, a dew point temperature measurement of the contents of a cylinder of gas provides a measure of the purity of the gas in the cylinder. In fact, the industrial applications for dew point temperature measuring and dew point temperature measuring apparatus are numerous and varied.

One known method of measuring the dew point temperature of a moist gas involves passing a flow of gas over a mirror surface. A light source, such as a light emitting diode (L.E.D.) is directed towards the mirror surface and a photosensitive detector is positioned so as to detect light, emitted by the L.E.D., which is reflected from the mirror surface. A cooling system is used to reduce progressively the temperature of the mirror surface until moisture in the moist gas condenses to form dew or frost on the mirror surface. Dew (or frost) forming on the mirror surface in the path of light emitted from the L.E.D. causes the light to be deflected (or scattered) from its original path such that the amount of light detected by the photodiode is reduced. By providing a servo loop between the photodiode and the cooling system, the temperature of the mirror may be controlled in order to maintain it at an equilibrium temperature where the rates of condensation and evaporation of water molecules onto or from the mirror surface are equal and a constant mass of water (or frost) is maintained on the mirror thereby providing a constant level of scattering and hence of the light level detected. This occurs at the dew point temperature. This type of apparatus is often referred to as a chilled mirror hygrometer.

However, this method has the disadvantage of requiring a sufficient amount of moisture to condense on the mirror in order to provide a reliably detectable scattering of the light emitted by the L.E.D. Where the moist gas being measured is relatively dry, for example having a moisture content of 10 parts per million of water molecules (or below), it can take a considerable time, typically several minutes, for enough condensation to occur in order to achieve a reduced reading from the photodiode detector. As a result, the progressively reducing temperature of the mirror may have decreased to well below the dew point temperature before a sufficient amount of condensation has occurred. This limits the accuracy with which the dew point temperature an be determined over relatively short periods of time due to the relatively large oscillations of the mirror temperature above and below the dew point temperature before an equilibrium state is reached. Thus, measurements of the dew point temperature can take upwards of one hour to be accurately obtained where the moisture content of the gas is very low, say between ten parts per million and one tenth parts per million (corresponding to dew point temperature between approximately −60° C. and −100° C.). Additionally, problems can occur where dust or other particles settle on the mirror and cause the light from the L.E.D. to be scattered or deflected away from its original path between the L.E.D. and the photodiode detector, leading to inaccurate measurements of the dew point temperature. Furthermore, where, the gas whose moisture content is to be measured itself condenses at a temperature which is above the dew point of the moist gas, (e.g. certain hydrocarbon gases) problems will occur due to the gas molecules condensing on the mirror and deflecting/scattering the light before the mirror even reaches the dew point temperature of the moist gas.

Under certain vapour pressure and temperature conditions pure water cooled below 0° C. can become a supercooled liquid. Another disadvantage of the above-described "chilled mirror hygrometer" method occurs when attempting to measure dew points below 0° C. (i.e. "frost points"). The chilled mirror hygrometer is unable to detect the condensation of individual water molecules which occurs at the frost point temperature when individual water molecules attach themselves to the mirror. Because of their lack of mobility these molecules will have an equilibrium water vapour pressure which corresponds to ice as opposed to super cooled water. The mirror will continue to cool until the water molecules bond themselves into groups of molecules large enough to scatter light. If the groups of molecules arrange themselves into ice or frost crystals then the chilled mirror temperature will eventually reach a state of equilibrium at a temperature corresponding to the frost point temperature of the gas. However the individual water molecules may arrange themselves into groups of super cooled liquid which would give the individual water molecules greater mobility. In the latter case the chilled mirror temperature will eventually stabilise at the dew point temperature which can be several degrees lower than the frost point temperature for a given water vapour pressure. As both pure water and ice are good insulators of electricity and it is therefore not possible to distinguish between pure water and ice by electronic means, the chilled mirror hygrometer operator needs to use a microscope focussed on the mirror to determine whether ice or water has been formed if accurate readings are required when measuring the dew or frost point temperature in clean air or gas.

SUMMARY OF THE INVENTION

It is an object of the present invention to provide a method of measuring the dew point temperature of a moist gas which avoids or minimises one or more of the above disadvantages.

According to a first aspect of the invention, a method of measuring the dew point temperature of a moist gas comprises the steps of: passing a flow of moist gas over a surface; measuring the temperature of said surface; positioning a moisture sensor in the flow of gas, downstream of said surface; applying cooling to the surface so as to reduce progressively the temperature of the surface; while the surface is being cooled, monitoring moisture content of the gas downstream of said surface; detecting a decrease in moisture content of the gas downstream of said surface due to moisture condensation from the moist gas at the dew point temperature thereof, and using the detected decrease in moisture content due to said moisture condensation to control the temperature being measured so as to obtain a dew point temperature. The detected decrease in moisture content may be used to control measurement of the temperature of said surface so as to obtain a dew point temperature. Preferably, the detected decrease in moisture content due to said moisture condensation is used to control cooling of said surface so as to maintain said surface substantially at the dew point temperature of said moist gas at least during a dew point temperature measuring period so as to obtain a dew point temperature.

One advantage of the present invention is that the method is selectively sensitive to the condensing of water molecules thereby avoiding or reducing the risk of inaccuracies resulting from the presence of dust, and/or condensation of the gas whose moisture content is being measured. Moreover by using highly sensitive moisture sensors it is possible to obtain very fast, typically within seconds, detection of changes in moisture content thereby enabling the rapid measurement of dew point temperature which can be effected in a variety of ways. Moreover, even very small changes in moisture content can be detected so that at dew points below 0° C. the condensing of very small amounts of frost can be detected very quickly, typically within seconds, prior to the formation of any ice crystals or supercooled water droplets.

In a particularly simple embodiment of the invention a single direct value for the dew point temperature may be obtained by simply measuring the temperature of the surface at or immediately after detection of the decrease in the moisture content due to moisture condensation. This provides an instantaneous "spot check" value for the dew point temperature. In a preferred embodiment, the application of cooling to said surface is controlled in response to the detection of the decrease in moisture content due to moisture condensation. The cooled surface is subsequently allowed to increase in temperature e.g. simply by reducing or discontinuing cooling to allow warming by the gas flow, or if desired by also supplying external heating. By continuing to monitor the moisture content of the gas downstream of the surface after the cooling of the surface has ceased, the moisture content can be monitored as it then increases due to evaporation of the condensed moisture from the surface and subsequently decreases to a final moisture content substantially equal to the moisture content prior to the decrease due to moisture condensation. Preferably, the application of cooling to said surface is then recommenced in response to the detection of the final moisture content to begin another moisture condensation and evaporation cycle. The moisture condensation and evaporation cycle may be carried out at least twice and, preferably, is carried out several times. An average value for the dew point temperature of the moist gas may be obtained by calculating the average temperature of the surface over one such moisture condensation and evaporation cycle. Preferably, the average value of the dew point temperature is obtained by calculating the average temperature of the surface over several such cycles. The average temperature of the cooling surface may be determined by any suitable technique including simply determining the midpoint of the upper and lower temperature peaks of said cycle, or by more sophisticated analysis of the form of the temperature curve cycles as discussed further hereinbelow. Whichever particular method is used though, it is a particular advantage of the present invention that by using a rapid and sensitive detection of condensation onto or evaporation from the surface with changing temperature thereof, the temperature range of the cyclic temperature variation of the surface can be substantially restricted as compared with the prior art, typically to less than 1° C., for example to around ±0.1° C. relative to the actual dew point temperature thereby enabling significantly more accurate measurements to be made.

A further preferred form of the invention includes monitoring the moisture content of the gas upstream of the surface. Monitoring the difference between the moisture content of the gas upstream of the surface and the moisture content of the gas downstream of the surface enables a decrease in the moisture content of the gas downstream of the surface to be detected independently of any underlying changes in moisture content of the moist gas being tested i.e. changes in moisture content not due to condensation onto or evaporation from said surface due to changes in the temperature of the surface.

As already indicated above it is a particular advantage of the invention that measurements may be made substantially more quickly than with previously known systems—typically within seconds rather than several minutes. In certain cases though there is a need for even more rapid measurement in order to detect changes occurring within fractions of a second which may even be measured in milliseconds, and/or to detect very small changes in moisture content measured in fractions of 1 ppm.

In a second aspect the present invention also provides a method of measuring dewpoint temperature comprising the steps of providing a moisture sensor, and processor means programmed to convert the moisture sensor output into a dewpoint temperature reading value, which method includes the steps of calibrating the processor means by measuring the dewpoint temperature of a gas sample, and comparing said dewpoint temperature reading measurement with said dewpoint temperature reading value and re-programming said processor means where said dew point temperature measurement and said dew point temperature reading do not match.

Preferably the dewpoint temperature measurement used to calibrate the moisture sensor output processor means is carried out, advantageously more or less continuously, using a method and apparatus of the invention. It will be appreciated though that other forms of dewpoint temperature measuring apparatus can also be used for the purposes of calibration e.g. a conventional optical system, though these are generally less preferred for the reasons mentioned hereinbefore.

With this type of dewpoint measurement method (and corresponding apparatus), it is possible to increase significantly the sensitivity of dewpoint temperature variations even more—typically from ±0.1° C. to ±0.001° C. Furthermore changes in moisture content occurring in time periods of as little as several milliseconds can be detected. This enables the achievement of substantially "real-time" dew point temperature measurement.

According to a third aspect of the invention, an apparatus for measuring the dew point temperature of a moist gas comprises a surface, a cooling system formed and arranged for applying cooling to the surface so as to reduce progressively the temperature of the surface, a moisture sensor for monitoring moisture content of gas which passes over said surface; detector means for detecting a decrease in the monitored moisture content of the gas due to moisture condensation of the moist gas at the dew point temperature thereof, and temperature measuring means for measuring the temperature of said surface.

Preferably, the apparatus further comprises cooling control means for controlling cooling of said surface so as to maintain said surface substantially at the dew point temperature of said moist gas at least during a dewpoint temperature measuring period so as to obtain a dewpoint temperature.

The cooling control means may comprise a feedback loop between the detector means and the cooling system.

The detector means may be adapted to send a signal, via the feedback loop, to the cooling system upon detection by the detector means, of a decrease in moisture content due to moisture condensation from the moist gas. The cooling system may be adapted to receive the signal from the detector means and, upon receiving the signal, stop (or reduce) cooling the surface. Upon receiving the signal, the cooling system is preferably automatically switched off so as to stop reducing the temperature of the surface. Alternatively, the cooling system may be provided with heating means which are adapted to commence heating the surface, so as to increase the temperature of the surface, upon receiving the signal from the detector means. The cooling system may be adapted to receive a further signal from the detector means, upon receipt of which signal the cooling system is automatically switched back on so as to again reduce progressively the temperature of the surface. The cooling system may also be adapted to cause the heating means to stop heating the surface upon receipt of the further signal by the cooling system, if heating means are provided.

The detector means may comprise a switch. Alternatively the detector means may comprise a three-term controller. The apparatus may further comprise signal processing means for processing temperature measurements of said surface. Preferably, the signal processing means is adapted to calculate an average value of the temperature of said surface during the dewpoint temperature measuring period, which average value is the measured dewpoint temperature.

In accordance with the present invention there may be used just a single moisture sensor. If desired though there may also be used a second moisture sensor for monitoring moisture content of gas travelling towards the surface. The signal processing means may be adapted to process the moisture contents monitored by the first and second moisture sensors. Preferably the signal processing means is adapted to compare the moisture content monitored by the first moisture sensor with the moisture content monitored by the second sensor, or vice versa, in order to detect underlying changes in the gas moisture content (i.e. changes not associated with condensation to or evaporation from the cooled surface).

The detector means, the cooling control means and the signal processing means may all be provided in a microprocessor. The microprocessor is advantageously pre-programmed to enable the apparatus to operate in one or more different operating modes. For example, the microprocessor may be programmed so as to calibrate one or each of the moisture sensors to give instanteous (for example, within a few milliseconds) dew point temperature values for measured moisture content readings. Thus, for example, where continuous cooling of said cooled surface is impractical or where dewpoint temperatures to be measured are beyond the cooling capability of the cooling system of the apparatus, estimated dew point temperatures can be obtained. The calibration may be achieved using data stored whilst the apparatus is functioning within the cooling capability of the cooling system during a series of dew point temperature measurements. Calibration of at least one of the moisture sensors to give instantaneous dew point temperature values in this way enables substantially "real time" dew point temperature measurements to be obtained.

Where both sensors are calibrated to give instantaneous dew point temperatures, the microprocessor may be programmed to identify a sudden failure of either of the two moisture sensors and to continue to display dew point temperature readings based on the moisture level readings obtained from the other sensor. The apparatus is advantageously provided with fault indicator means for displaying a fault indication until the faulty sensor has been replaced.

The second moisture sensor may be a pre-calibrated moisture sensor, calibrated to obtain direct readings of the dew point temperature of a moist gas. The signal processing means may comprise a servosystem for monitoring the dew point temperature measurement obtained from the pre-calibrated moisture sensor. Comparison means may be provided for comparing this dewpoint measurement with the calculated average value of the temperature of said surface. The servo system and the comparison means may be provided in the microprocessor. The servosystem may be formed and arranged to re-calibrate the pre-calibrated moisture sensor if the compared dewpoint measurement and the calculated average value of the temperature of the surface do not match. The servosystem conveniently uses suitable computer software for carrying out the re-calibration of the pre-calibrated moisture sensor.

The microprocessor may also be programmed so that in the event of a failure of the temperature measuring means and/or of the cooling system, the apparatus will continue to operate by displaying dew point readings obtained from the calibrated second (upstream) sensor.

The microprocessor may be programmed so as to provide a "spot check" mode in which the microprocessor is programmed to display the temperature of said surface at the onset of moisture condensation as an unconfirmed dew point temperature measurement. Following the expiry of a dew point temperature measuring period the unconfirmed dew point temperature reading is confirmed or corrected by calculating the average temperature of said surface during the dew point temperature measuring period. Rapid spot check readings are often required during applications such as, for example, the automatic filling of gas cylinders.

In accordance with the present invention there may be used a variety of rapidly reacting sensitive moisture sensing systems which provide an electrical signal. Preferably there is used a moisture sensor which produces a direct electrical response to changes in moisture level, for example a change in electrical capacitance. Suitable sensors of this type are known in the art and can be calibrated to give read-out values in terms of parts per million (ppm) moisture. One example comprises a layer of porous silicon oxide and a non-porous silica wafer. Alternatively, the sensor may comprise a layer of porous aluminium oxide and a non-porous aluminium wafer. Such sensors are capable of measuring moisture contents down to one part per million and below and are rapidly responsive to minute changes in moisture content levels. Alternatively, the or each moisture sensor may be of the oscillating crystal type.

The use of such moisture sensors enables a rapidly responsive system to be achieved in which the temperature of said surface can be rapidly oscillated above and below the dew point temperature.

The temperature sensor may be of the platinum resistance type and is preferably mounted in the cooled surface.

The cooling system may comprise a thermoelectric heat pump which may incorporate a Peltier device. Said surface may comprise a layer of material having a high heat conductivity, said layer being in contact with the heat pump. Alternatively, said surface may form part of a wall of a hollow tube or pipe through which a flow of moist gas may be passed. A portion of said tube or pipe may be bent or coiled. The cooling system may comprise a reservoir of liquid refrigerant in which the bent or coiled portion of the tube or pipe is submerged, the temperature of the reservoir of fluid being controlled by the amount of electric current which is passed through an electrically conductive element submerged in the fluid or by a thermoelectric heat pump in thermal contact with the liquid refrigerant. The cooling system may alternatively utilise gas expansion in order to achieve cooling. A portion of said tube or pipe may be immersed in a chamber into which a gas under high pressure is allowed to expand though an orifice so as to produce a cooling effect on said portion of the tube or pipe. Said portion is preferably coiled.

Advantageously, the apparatus according to the invention is portable.

Where very low dew points are to be measured, more than one of the described types of cooling system may be employed in order to achieve sufficiently low temperatures of said surface.

The apparatus may further include an additional temperature measuring means, readings from which may be utilised by the microprocessor to express dew point temperature readings obtained from the apparatus in terms of relative humidity. The additional temperature measuring means is preferably disposed in the moist gas whose dew point is being monitored, at a location remote from said surface being cooled.

Preferred embodiments of the invention will now be described by way of example only and with reference to the accompanying drawings in which:

BRIEF DESCRIPTION OF THE DRAWINGS

FIG. 5 shows a schematic calibration curve of a pre-calibrated moisture sensor;

FIG. 6 shows an alternative dewpoint temperature measuring apparatus, in schematic;

FIG. 7 shows another embodiment of dew point temperature apparatus in accordance with the invention, in schematic;

FIG. 8(b) is a cross-sectional view of the apparatus of FIG. 7, taken along the line C-C';

DESCRIPTION OF ILLUSTRATED EMBODIMENT

Figure 1:
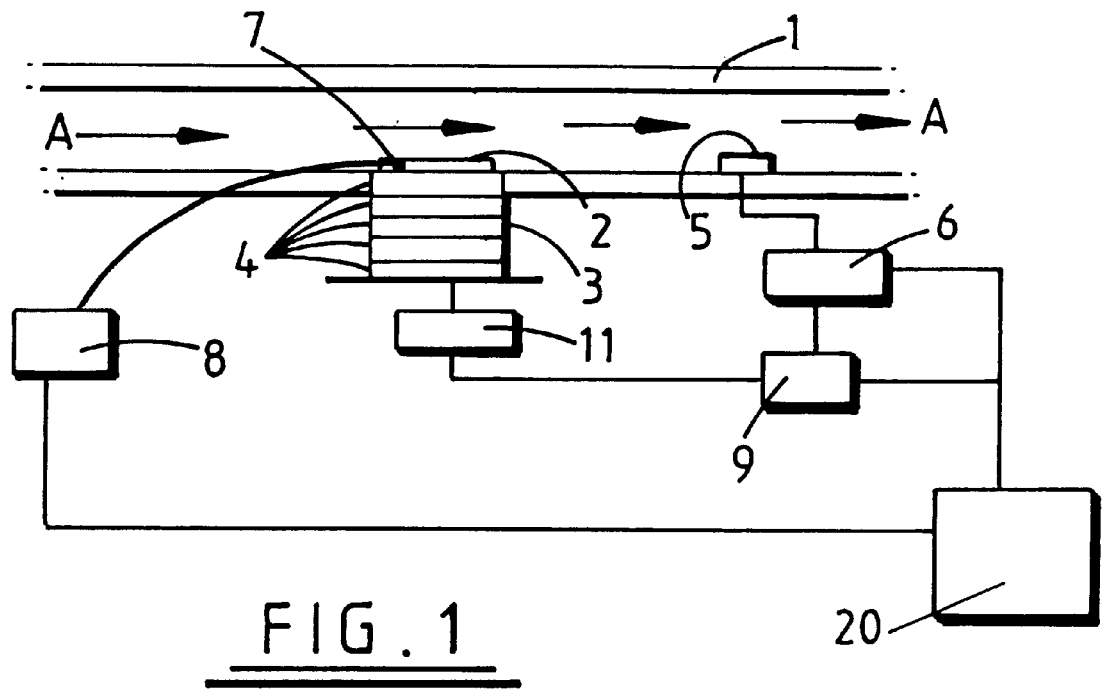
FIG. 1 is a schematic illustration of an apparatus for measuring the dewpoint temperature of a moist gas, according to the invention.
Figure 2:
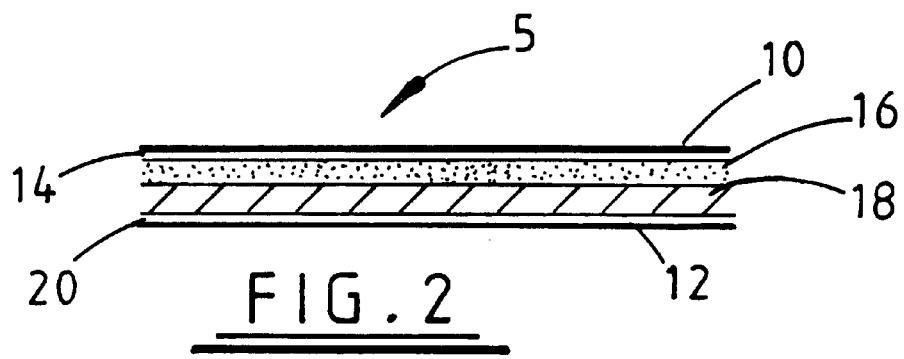
FIG. 2 is a schematic cross-sectional side view of a moisture sensor incorporated in the apparatus of FIG. 1.

FIG. 1 illustrates schematically an apparatus for measuring the dewpoint temperature of a moist gas. The gas, which is in this embodiment moist air, A, flows along the inside of a pipe 1. The moist air, A, passes over, making contact with, a surface 2 of platinum film which is mounted on a thermoelectric heat pump unit 3 which is mounted in the wall of the pipe 1. The heat pump unit contains thermoelectric modules 4 incorporating Peltier crystals and is powered electrically via a current supply 11 in order to cool the surface 2 so as to reduce progressively the temperature of the surface 2. A moisture sensor 5 is mounted downstream of the surface 2 and monitors the moisture content of air in a region generally above the sensor by measuring the moisture content of moist air with which the sensor is in contact. The sensor 5 is of the capacitance type and measures changes in capacitance due to moisture present in the air. FIG. 2 shows, in detail, a schematic cross-section (extremely magnified) of such a sensor. The sensor comprises an upper, outer layer 10 of gold (Au) film and a lower, outer layer 12 of gold film. Immediately below the upper film of gold is a layer 14 of chromium (Cr) film and, below that, a layer 16 of porous silicon oxide (SiO). Beneath the layer 16 of silicon oxide is a wafer 18 of non-porous silicone (Si). Below the silicon wafer is another layer 20 of chromium film, deposited on the lower, outer film of gold. The complete sensor 5 acts as a capacitor. Water molecules in the moist air A pass through the upper layers of gold and chromium film and deposit themselves in the layer 16 of porous silicon oxide, thus causing a change in the capacitance between the two gold layers.

The change in capacitance detected by the sensor 5 is converted to an analogue or, alternatively, a digital signal by a convertor 6 which monitors changes in frequency in a circuit due to changes in capacitance of the sensor 5. A temperature sensor 7 of the platinum resistance type is incorporated in the surface 2 and resistance measurements are converted to temperature readings in a control unit 8.

Figure 3:
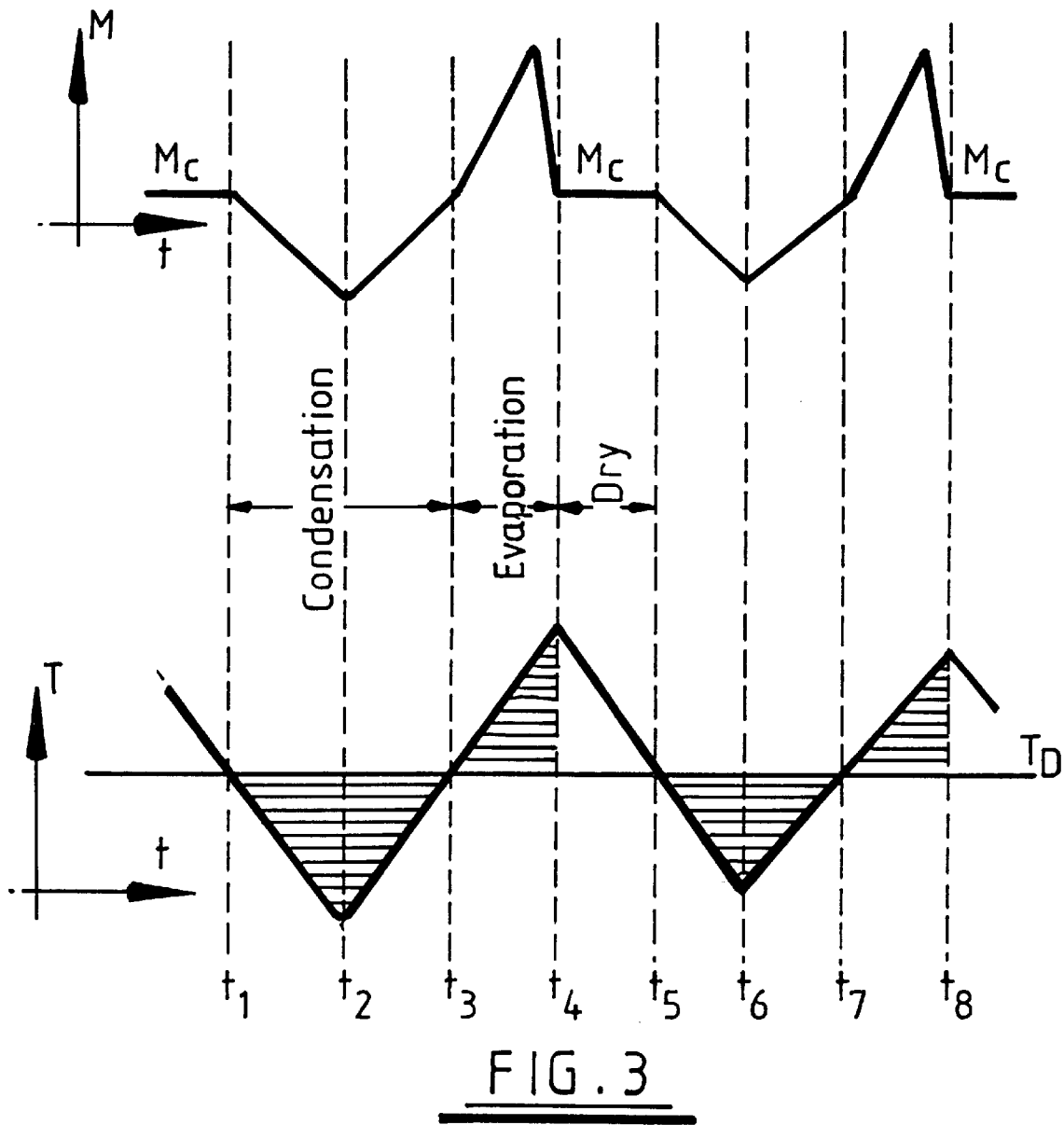
FIG. 3 shows a schematic graph of "moisture" against "time" obtained from the moisture sensor of FIG. 2 incorporated in the apparatus of FIG. 1 and a schematic graph of "temperature" against "time" obtained from a temperature sensor incorporated in the apparatus of FIG. 1.

As the temperature of surface 2 is reduced progressively, the surface will eventually reach a temperature at which moisture in the moist air A will condense out onto the surface 2. This happens when the surface 2 reaches dewpoint temperature $T_D$ of the moist air passing over the surface 2. When this condensation has occurred, the moisture sensor 5 which is monitoring the moisture content of the moist air downstream of the surface 2, will sense a decrease in moisture content below a previously steady moisture content $M_C$ (corresponding to the moisture content of the air before any moisture condensed out onto the surface 2). This decrease is due to the decreasing concentration of water molecules in the air sample passing over the sensor 5 due to some molecules having condensed out onto the surface 2 upstream of the sensor 5. A detector unit 9 which receives the output from the convertor 6 detects this decrease in the moisture content. The detector unit 9 is linked, in a feedback loop, to current supply 11. Upon detecting the decrease the detector 9 terminates the supply of current to the heat pump unit 3 so as to stop reducing the temperature of the surface 2, which has by now reduced below the dewpoint temperature $T_D$. The surface subsequently begins to warm up progressively (due to its contact with the flow of moist air A and the surrounding ambient temperature). When the temperature T of the surface 2 reaches and exceeds the dewpoint temperature $T_D$, the condensed water on the surface 2 evaporates, causing a subsequent rise in moisture content monitored by the sensor 5 downstream of the surface 2. FIG. 3 illustrates the moisture M and temperature T curves (plotted against time, t) which are recorded by a microprocessor 20 which is connected to the convertor 6, the detector 9 and the control unit 8. At time $t_4$ all the condensation has evaporated from the surface 2 and the moisture content reading from the sensor 5 has dropped back to its original level $M_C$. At this point the detector unit re-commences the supply of current to the heat pump unit 3 so as to start reducing the temperature of the surface 2 once more, thus starting another similar moisture condensation and evaporation cycle. As shown in FIG. 3, the period of this cycle is equal to $(t_5-t_1)$.

After one condensation and evaporation cycle, the microprocessor, incorporating a signal processor, calculates the average temperature of the surface 2 over the cycle which has taken place. The curves shown in FIG. 3 are exaggerated for clarity, but in reality the peaks and troughs in temperature T above and below the dewpoint temperature $T_D$ only have an amplitude of approximately 0.1° C. or less. The calculated average temperature provides a measured value of the dew point temperature. Where readings are obtained over several cycles the average temperature of the surface 2 over two or more such cycles may alternatively be calculated to obtain the measured dew point temperature.

In one embodiment, the detector unit 9 is a 3-term controller which controls the current to the heat pump unit 3 so as to maintain the temperature T of the surface 2 substantially at the dewpoint temperature $T_D$ throughout the plurality of condensation and evaporation cycles, thus enabling an extremely accurate determination of the dewpoint temperature to be made.

Figure 4:
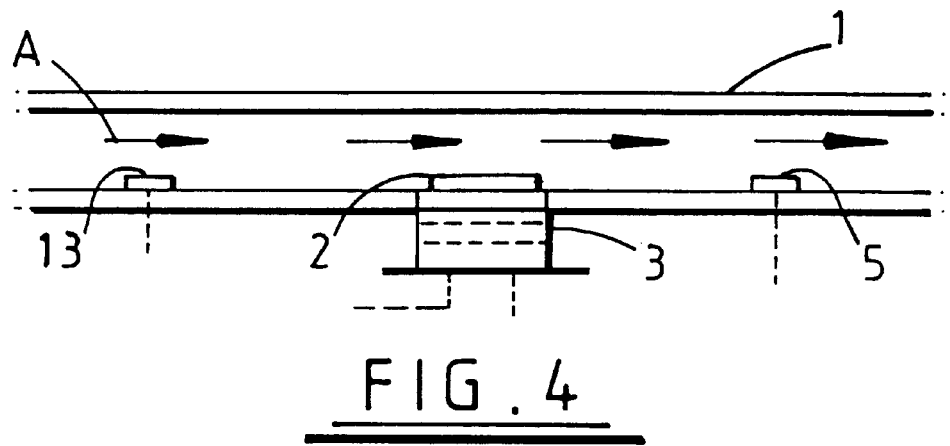
FIG. 4 is a schematic fragmentary view of an alternative embodiment of the invention.

In a modified embodiment of the invention, illustrated schematically in FIG. 4, the arrangement comprises a further moisture sensor 13 disposed upstream of the surface 2 and of the same type as the moisture sensor 5 disposed downstream of the surface 2. The capacitance output of the upstream sensor 13 is converted to an analogue or digital signal by a convertor (not shown), the output of the convertor being fed to the microprocessor 20. In this embodiment, the signal from the convertor 6 for the downstream sensor 5 is fed directly to the microprocessor 20. By subtracting the monitored moisture content M of one of the sensors 5, 13 from the monitored moisture content of the other one of the sensors (taking an appropriate time lag into account, if necessary), the resultant difference signal is thus unaffected by any changes in moisture content of the moist air A which may occur which are not due to condensation or evaporation of moisture from the surface e.g. if the air flow is subject to a rapidly varying environment prior to entering the pipe 1, causing its moisture content to vary rapidly. The difference signal is then fed to a detector unit, which may be incorporated in the microprocessor, and the dewpoint temperature is measured as before, the difference signal following the same moisture curve M as that shown in FIG. 3.

The sensor 13 is pre-calibrated so as to enable a value of the dewpoint temperature to be obtained directly from a capacitance reading obtained from the sensor 13. The sensor may be pre-calibrated using any known technique for measuring the dewpoint temperature of a moist gas, although preferably it is calibrated using the apparatus of FIG. 1. FIG. 5 illustrates a calibration curve for the pre-calibrated sensor 13, of capacitance against dewpoint temperature. By using the pre-calibrated sensor 13 in combination with the dewpoint temperature measuring apparatus of FIG. 1, the value of the dewpoint $T_D$ obtained directly from the upstream sensor 13 can be compared with the value $T_D$ obtained using the apparatus of FIG. 1. This comparison is carried out in the microprocessor which may be suitably programmed to carry out re-calibration or adjustment of the upstream sensor calibration curve if the compared values do not correspond or are substantially different. The data used to perform this recalibration is preferably that stored by the microprocessor and which represents the most recent comparative readings between the direct reading or precalibrated sensor 13 and the downstream sensor. However, the pre-calibrated sensor 13 could be used in combination instead with any other known dewpoint measuring apparatus 30 to achieve this re-calibration system, as illustrated by FIG. 6. The comparison of the dew point temperature measurements would be carried out in a microprocessor or other comparison and re-calibration apparatus 32.

Figure 8A:
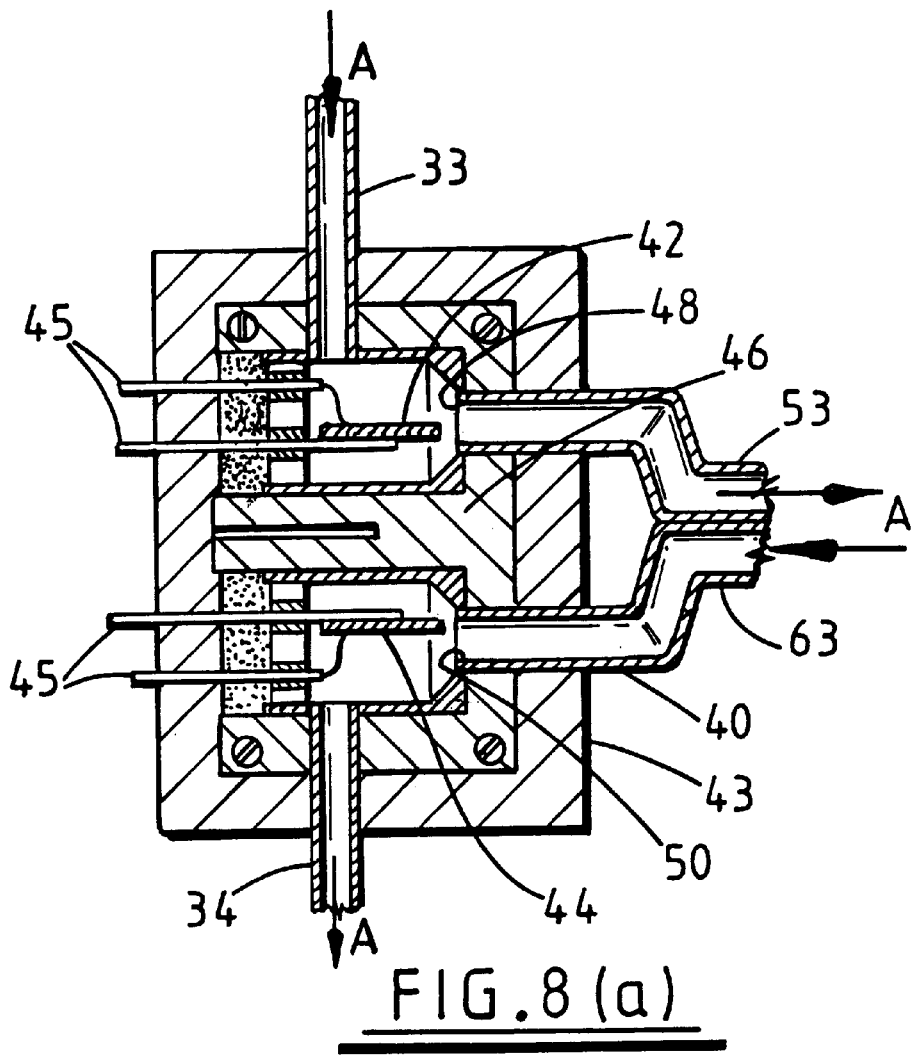
FIG. 8(a) is a magnified view of ringed portion D of the apparatus of FIG. 7.

FIG. 7 shows another embodiment of the invention in which the surface to be cooled forms part of an inner surface (not shown) of the wall of a thin stainless steel tube 40 through which tube a sample of the gas to be monitored flows. As shown in detail in FIG. 8(a), in this embodiment an upstream moisture sensor 42 and a downstream-moisture sensor 44 are mounted in an aluminium block housing 46 into and out of which a flow of gas A to be monitored may pass via an inlet 33 and an outlet 34 respectively. The gas A may, for example, be flowing through a gas line or pipe (not shown) in which the housing 46 and moisture sensors 42, 44 are positioned. The upstream and downstream moisture sensors 42, 44 are located adjacent to an inlet 48 and an outlet 50 respectively of the thin tube 40. The housing 46 is machined from two halves and bolted together. Insulation material 43 surrounds the housing 46.

As shown in FIG. 7 the tube 40 has a coiled section 52 which is housed in an enclosure 54 containing a thermally conductive liquid 51. A base wall of the coil enclosure 54 is defined by an upper surface of a Peltier crystal thermoelectric heat pump unit 56 which is electrically connected 58 to a microprocessor 60 which is programmed to control the operation of the thermoelectric unit 56.

From the inlet 48 of the thin tube 40, the tube 40 extends along a section 53 towards the enclosure 54 where it enters the enclosure through an upper wall thereof and spirals down to form the coiled section 52 a lower end of which is located close to the Peltier crystal unit. The tube 40 then passes straight up the inside of the enclosure 54 and exits therefrom through the upper wall thereof where it extends along a section 63 to the sensor housing 46 where it terminates in the outlet 50. A temperature sensor 62 which is electrically connected 59 to the microprocessor 60 is mounted on a lower portion 64 of the coiled section 52 of the tube 40. Each moisture sensor 42, 44 is electrically connected, via gold plated pins 45, to electronic circuitry 65, 66 which is electrically connected to the microprocessor 60 which, in turn, is connected to a display 61 for displaying readings taken from the moisture and temperature sensors and for displaying measured dew point temperatures.

Thermal insulation material 64 surrounds the coil enclosure 54 and the Peltier crystal unit 56 is mounted on a heat sink 69. As shown in FIG. 8(*b*), the sections 53, 63 of the tube 40 between the coiled section 52 and the inlet 48 and outlet 50 respectively are lagged with a heat conducting material 55 which is surrounded by an outer tubing 67 which in turn is covered with thermal insulation material 57 to prevent condensation occurring on the outside of the tube sections 53, 63.

The housing 46 in which the moisture sensors 42, 44 are mounted is in the form of a metal block which helps to maintain the two sensors at substantially the same temperature. Where dew point temperatures above the ambient temperature of the housing 46 are to be measured, the housing 46 and the tube sections 53, 63 are heated so as to prevent condensation thereon.

The moisture sensors 42, 44 are of the capacitance type described previously in relation to the apparatus of FIG. 1, having a hygroscopic dielectric constructed from silicon oxide. These moisture sensors have a very fast response time and good discrimination potential; particularly at low moisture levels. The number of water molecules held in the pores of the dielectric is dependent on the water vapour pressure in contact with the active side of the sensor and on the temperature of the sensor. The change in the sample gas moisture concentration will cause an immediate change in the sensor capacitance value.

The associated sensor circuitry 65, 66 serves to convert sensor capacitance values into frequency. As the moisture content of the sample gas changes the output frequency transmitted by these circuits will also change.

The temperature sensor 62 is carefully positioned and thermally bonded to the coiled section 52 so that it will give a reading equal to the temperature within the coldest part of the cooling coil. Any uncertainty of temperature measurement will add the same uncertainty of dew point measurement.

When the apparatus of FIGS. 7 and 8 is powered up for the first time the microprocessor contains no data relating to the sensors 42, 44 which initially need to be purged with ambient air having a dew point temperature which could be anything from 5–20° C. (The actual level is unimportant because both sensors are purged with the same air). After a few minutes when the sensors are at equilibrium with ambient air the micro processor stores data for each sensor. The ambient air purge is then replaced with dried air or gas from a cylinder. Information on the dry air or gas is unimportant providing it has a moisture content significantly below that of the ambient air. This allows the micro processor to confirm that both sensors are functional and to obtain a rough measure of the sensitivity of each sensor. The dry air is then mixed with increasing amounts of ambient air to provide five different known moisture concentrations. Each concentration is purged through the instrument for at least one hour. At the end of the fifth the instrument is able to automatically calibrate the two silicon sensor to give read-out values in terms of moisture concentration (ppm moisture) where this is desired. This initial calibration will be stored and may also be used to detect any drift or degradation of the sensors 42, 44 during the working life of the apparatus by comparison with the readings taken by the micro processor during normal moisture content fluctuations of a sample gas. In the event that the sample gas never changes its moisture concentration (except at the dew point temperature) the above described test may be repeated to enable the micro processor to carry out a full sensor recalibration automatically.

The operation of the apparatus of FIGS. 7 and 8 is similar to that of FIGS. 1 and 4, Peltier crystal unit 56 being controlled by the microprocessor 60 so as to vary the temperature of the coiled section 52 of the tube 40 over one or more moisture condensation and evaporation cycles, of the type shown in FIG. 3, for the moist gas passing through the coiled section 52 of the tube 40 and the temperature reading T being taken from the temperature sensor 62. The differential signal obtained by subtracting one moisture sensor frequency signal from the other moisture sensor frequency signal at any given time is taken as the moisture reading M.

In order to measure the dew point temperature of a particular moist gas, the inlet 48 and outlet 50 of the tube 40 are connected to a gas line to be monitored and the tube 40 is purged with a small gas flow rate of about 100 mls per minute. The flow rate selected is not critical to the operation but it should be noted that the dew point reading obtained is dependent on the pressure contained within the condensing coil. If dew point temperatures at line pressures are required then a flow control valve should be located on the outlet 50 of the tube 40.

The microprocessor 60 is programmed to detect the start of the condensation cycle by an examination of the differential frequencies of the two moisture sensor 42, 44 and as soon as a decrease in moisture content (indicating the start of the condensation cycle) has been identified it will switch off the Peltier crystal unit 56 thereby causing the coil temperature T to rise. It will similarly recognise the start of the evaporation cycle and the completion of the evaporation cycle when both moisture sensors are again exposed to the same gas moisture content. In an alternative procedure, as soon as a decrease in moisture content is identified the current to the Peltier crystal unit 56 is reversed so that the heat pump operates to increase the temperature T of the coil.

A choice of operating mode is available. For continuous monitoring of dew point temperature a new condensation/evaporation cycle would be automatically started at the end of the previous cycle. So that rapid spot check readings may be obtained the microprocessor is programmed to display the coil temperature at the onset of condensation as an unconfirmed dew point reading. This reading could be about 0.1 deg. C lower than the true dew point temperature. Following the evaporation cycle the dew point reading would be corrected by averaging the condensation and evaporation temperatures. This reading could be displayed as a valid dew point. Positive identification of the evaporation cycle confirms that moisture has been condensed and subsequently evaporated thereby confirming that the displayed dew point reading is valid.

After each confirmed dew point reading the frequencies of the two moisture sensors during the cycle time when the coil was neither adding or substracting moisture from the sample gas are stored by the microprocessor. Periodic comparisons between present data and historical data can then be made. The sensor frequencies which correspond to known dew point temperatures would also be stored and periodically compared with previous data. After the instrument has been running for some time the microprocessor has the ability to:

1) Give statements of any change or derating of the moisture sensors.

2) Give an estimate of the useful life remaining before a moisture sensor needs to be replaced.

3) Provide an option of displaying live dew point signals based on the frequency of the upstream sensor 42 so that instantaneous moisture changes can be recorded regardless of the state of condensation/evaporation cycle. This mode of operation may be utilised when continuous cooling of the mirror is impractical or when dew point measurements are made which are beyond the maximum cooling capability of the coil. In the latter case the micro-processor utilises the data stored whilst the instrument was working within the coil cooling capability to extrapolate moisture sensor results beyond the maximum cooling capability.

4) In the event of a failure of the temperature measuring system or of the cooling system the apparatus can continue to run by displaying dew point readings taken from the upstream sensor 42. An alarm message would be given by the microprocessor 60 to identify the remedial action required.

5) In the event of a sudden failure of one of the moisture sensors 42, 44 the instrument will continue to display dew point readings based on the frequency readings relating to the good sensor. A fault indication would be displayed by the microprocessor until the faulty sensor has been replaced.

If the sample gas flowing through the tube 40 is highly corrosive to metal e.g. hydrogen chloride (HCl) gas or wet chlorine, instead of stainless steel the tube 40 is made of a more corrosive resistant material e.g. PTFE or Kevlar™. In order to overcome heat conductivity problems associated with such materials, the coiled section 52 of the tube 40 would be fitted inside a moulding of a material having a higher heat conductivity. The moisture sensor housing 46 would be made of glass, platinum, gold or silicon.

Figures 9A, 9B:
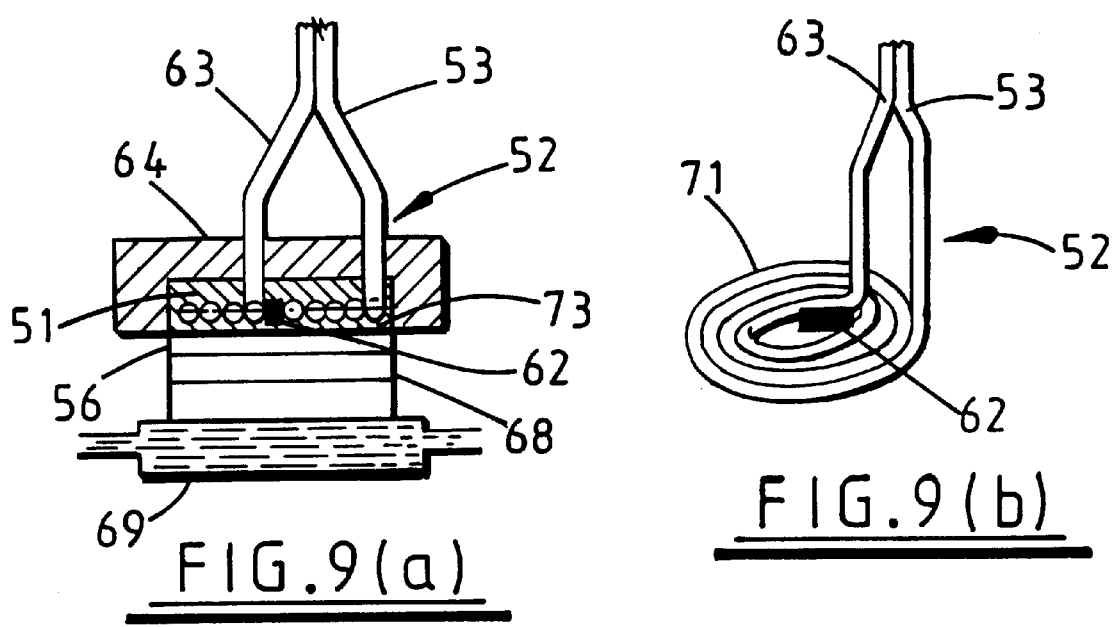
FIG. 9(a) is a sectional view of a portion of a modified version of the apparatus of FIG. 7, for measuring very low dew point temperatures.
FIG. 9(b) is a perspective view of a coiled portion of a tube of the apparatus of FIG. 9(a)

FIGS. 9(*a*) and 9(*b*) show a variation in the design of the coiled section 52 of the tube 40, for use when measuring very low dew or frost points, down to approximately −100° C. In this embodiment, the coiled section 52 comprises a substantially flat spiral portion 71 which is arranged substantially parallel to an upper surface 73 of a thermoelectric heat pump unit 56 which is the top one of a stack 68 of three such units. The spiral portion 71 is surrounded by a thermally conducting material 51 which thermally links the spiral portion to the heat pump unit 56. The thermally conducting material is surrounded by insulation material 64. A base of the heat pump unit 56 is mounted on a heat sink 69 through which flows a chilled liquid or gas e.g. liquid nitrogen which is allowed to boil off in order to provide additional cooling. The temperature sensor 62 is mounted to the spiral portion 71 at or near the centre of the spiral.

Figure 10:
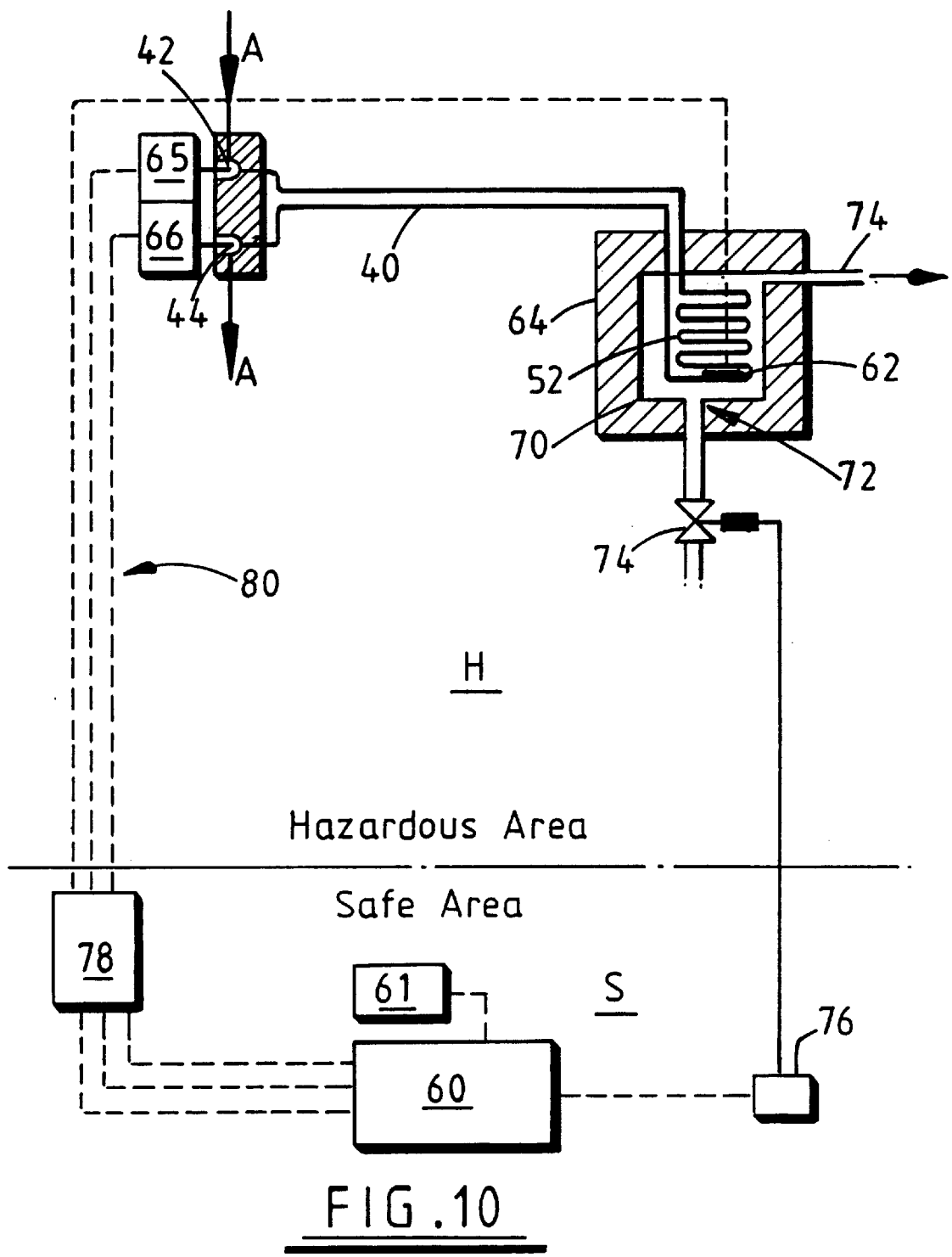
FIG. 10 is a schematic illustration of a modified version of the apparatus of FIG. 7.

FIG. 10 shows a modification of the embodiment of the invention shown in FIG. 7. In this embodiment the coiled section 52 of a tube 40, through which the sample moist gas passes, is cooled using gas expansion. The coiled section 52 is housed within a chamber 70 into which gas under pressure may flow through an orifice 72. An outlet 74 allows expanded gas to exit from the chamber 70. The chamber 70 is lagged in thermal insulation material 64. The flow of pressurised gas into the chamber 70 is controlled by an air operated valve 74 which, in turn is controlled by the microprocessor 60 via an electro-pneumatic convertor 76. Compressed air or gas is supplied to the orifice 72 when cooling of the coiled section 52 of the tube 40 is required. This arrangement is particularly suitable where the gas sample line is located in a hazardous environment (e.g. in an oil refinery) where the use of liquid refrigerant and heat pump units is undesirable because of the high power consumption and the possibility of high temperature surfaces. Electrical cables 80 (shown in hashed lines) are routed between the microprocessor 60 and the moisture sensors and temperature sensor 62 via an electrical barrier device 78 which includes Zener diodes for limiting the power transmitted into the hazardous area H should a fault occur with any of the circuitry incorporated in the apparatus. An operator can read/program the microprocessor from a safe area, S. The temperature of the coiled section 52 is also controlled from the safe area by the microprocessor.

The apparatus of FIG. 10 is portable, the compressed gas being supplied from a relatively small cylinder and electric power being supplied by an intrinsically safe battery.

Figure 11:
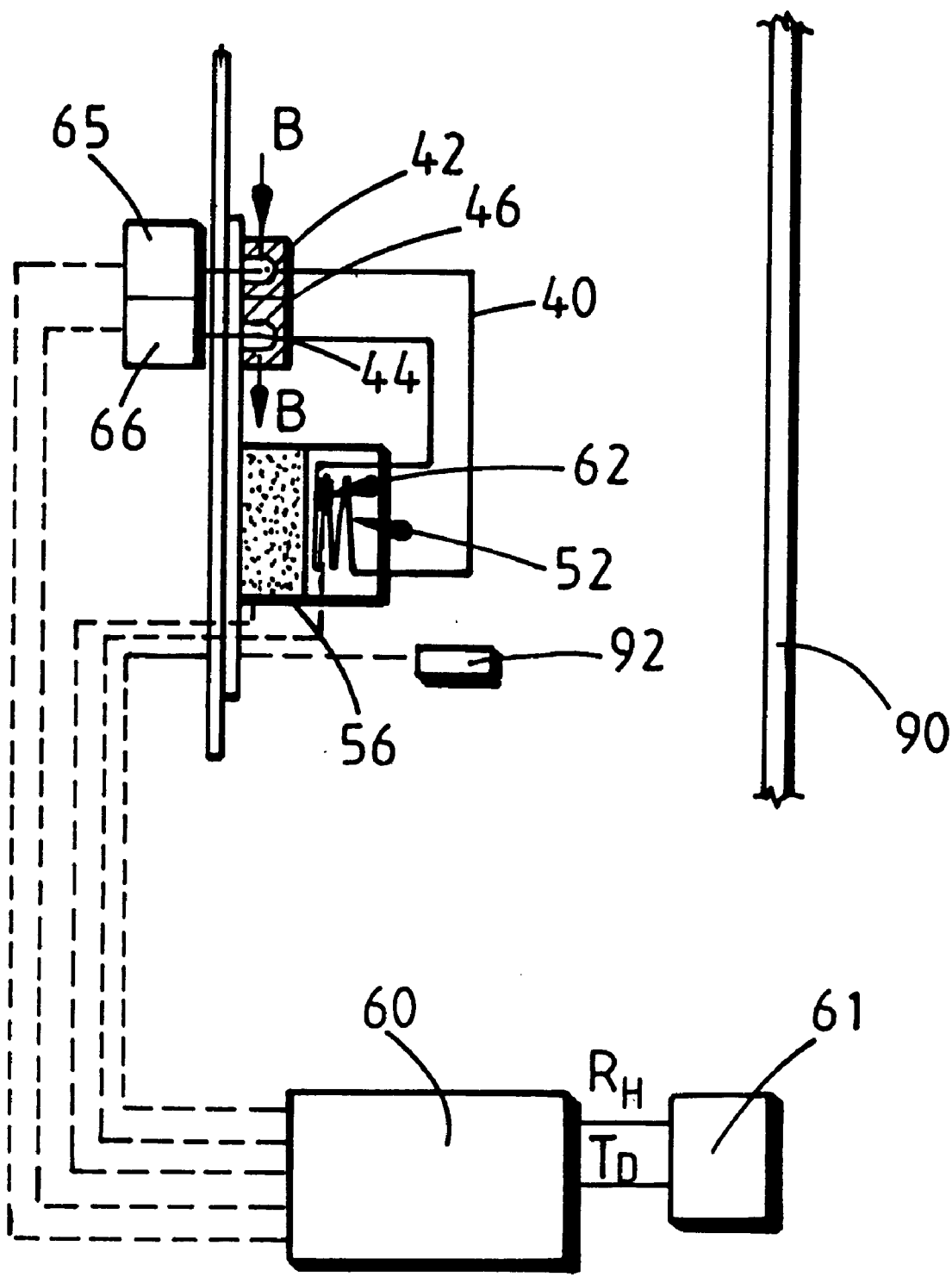
FIG. 11 is a schematic illustration of another modified version of the apparatus of FIG. 7.

FIG. 11 shows another modified version of the apparatus of FIG. 7, like parts being labelled by identical reference numerals. This arrangement is used when high humidity levels and dew points up to 100 deg. C. are to be measured. In this case the moisture sensors 42, 44 and coiled tube 40 are placed in the warm humid atmosphere to be monitored and the associated sensor circuits 65, 66 are located outside the chamber or duct 90 through which the humid gas sample B flows.

An additional temperature sensor 92 is provided, disposed in the interior of the duct 90 (shown in cross section) through which the flow B of the moist gas passes, remote from the coiled section 52 of the tube 40. Readings from the additional temperature sensor 92 are used by the microprocessor 60 where dew point temperature readings are required in terms of relative humidity (equal to the ratio of "partial vapour pressure" to "saturated vapour pressure". The dew point temperature, $T_D$ is directly related to the vapour pressure, and the saturated vapour pressure is dependent on the gas temperature). The relative humidity reading $R_H$ and/or dew point temperature reading $T_D$ are output to the display 61. This apparatus is therefore particularly suitable for measuring both dew point temperature and relative humidity in an oven, chamber or duct.

In the apparatus of any of FIGS. 7 to 11 there may be a suction pump (not shown) connected to the outlet 34 of the sensor housing 46 to ensure that the tube 40 is purged with a supply of the gas whose dew point is to be measured.

I claim:

1. A method of measuring the dew point temperature of a moist gas comprising the steps of:

passing a flow of moist gas (A) over a surface (2);

measuring the temperature of said surface;

positioning a moisture sensor (5) in the flow of gas, downstream of said surface;

applying cooling to the surface so as to reduce progressively the temperature (T) of the surface;

while the surface is being cooled, monitoring moisture content (M) of the gas downstream of said surface;

detecting a decrease in moisture content of the gas downstream of said surface due to moisture condensation from the moist gas at the dew point temperature thereof, and using the detected decrease in moisture content due to said moisture condensation to control the temperature being measured so as to obtain a dew point temperature ($T_D$).

2. A method according to claim 1 wherein the detected decrease in moisture content is used to control measurement of the temperature of said surface (2) so as to obtain a dew point temperature ($T_D$).

3. A method according to claim 1 wherein the detected decrease in moisture content (M) due to said moisture condensation is used to control cooling of said surface (2) so as to maintain said surface substantially at the dew point temperature ($T_D$) of said moist gas (A) at least during a dew point temperature measuring period.

4. A method according to claim 1 wherein a single value of the dew point temperature ($T_D$) is obtained by measuring the temperature of said surface (2) upon the detection of a decrease in moisture content (M) due to moisture condensation.

5. A method according to claim 1 wherein application of cooling to said surface (2) is reduced or discontinued upon the detection of a decrease in moisture content (M) due to moisture condensation.

6. A method according to claim 5 wherein, upon reduction or discontinuation of cooling, external heating is applied to said surface (2) so as to raise the temperature (T) of said surface (2).

7. A method according to claim 5 further including the step of continuing to monitor the moisture content of the gas downstream of said surface (2) as the moisture content (M) increases due to evaporation of condensed moisture from said surface and until the moisture content subsequently decreases to a final moisture content (Mc) substantially equal to the moisture content prior to the decrease due to moisture condensation.

8. A method according to claim 7 wherein application of cooling to said surface (2) is increased or recommenced upon detection of the final moisture content (Mc) and continued at least until a further decrease in moisture content below the final moisture content (Mc) is detected.

9. A method according to claim 8 wherein the dew point ($T_D$) is calculated as the average temperature of the surface (2) over one moisture condensation and evaporation cycle defined as the period between the commencement of the first decrease in moisture content and the commencement of said further decrease in moisture content below the final moisture content (Mc).

10. A method according to claim 8 wherein at least two consecutive moisture condensation and evaporation cycles are carried out, each cycle commencing with a decrease in moisture content due to moisture condensation, and the dew point temperature ($T_D$) is calculated as the average temperature of said surface (2) throughout the two or more consecutive cycles.

11. A method according to claim 7 wherein the temperature variation of said surface (2) is substantially restricted between 0.1° C. above and below the dew point temperature ($T_D$).

12. A method according to claim 1 further including the step of monitoring the moisture content of the gas upstream of said surface (2) and monitoring the difference between the moisture content of the gas downstream of said surface and the moisture content of the gas upstream of said surface.

13. A method of measuring dew point temperature comprising the steps of
providing a moisture sensor (5) and processor means (60) programmed to convert the moisture sensor output into a dew point temperature reading value, which method further includes calibrating the processor means by:
measuring the dew point temperature ($T_D$) of a gas sample,
using a method which includes the step of measuring the temperature of the gas sample as said gas sample crosses the dew point temperature ($T_D$) during cooling of said gas sample, comparing said dew point temperature measurement with said dew point temperature reading value, and re-programming said processor means where said dew point temperature measurement and said dew point temperature reading value do not match.

14. A method according to claim 13 wherein the dew point temperature ($T_D$) of the gas sample is measured using the method according to claim 1.

15. An apparatus for measuring the dew point temperature of a moist gas, the apparatus comprising a surface (2), a cooling system (3, 51, 56) formed and arranged for applying cooling to said surface so as to reduce progressively the temperature (T) of the surface, a moisture sensor (5, 44) for monitoring moisture content of a gas (A) which passes over said surface, downstream of said surface; detector means (9, 60) for detecting a decrease in the monitored moisture content (M) of the gas due to moisture condensation of the moist gas at the dew point temperature ($T_D$) thereof, and temperature measuring means (7, 62) for measuring the temperature of said surface.

16. An apparatus according to claim 15 further including cooling control means (6, 9, 60) for controlling of said surface (2) so as to maintain said surface substantially at the dew point temperature of said moist gas (A) at least during a dew point temperature measuring period so as to obtain a dew point temperature ($T_D$).

17. An apparatus according to claim 16 wherein the cooling control means comprises a feedback loop between the detector means (9) and the cooling system (3) and the detector means is adapted to send a signal, via the feedback loop, to the cooling system upon detection by the detector means (9) of a decrease in moisture content (M) due to moisture condensation from the moist gas (A).

18. An apparatus according to claim 16 wherein said detector means (9) comprises a three-term controller.

19. An apparatus according to claim 16 further including signal processing means (20, 60) programmed to process temperature measurements of said surface (2) so as to calculate an average value of the temperature (T) of said surface (2) during a dew point temperature measuring period and to output said average value as the measured dew point temperature ($T_D$).

20. An apparatus according to claim 19 wherein said detector means, cooling control means and signal processing means are together provided in the form of a microprocessor (60).

21. An apparatus according to claim 17 further including heating means formed and arranged to commence heating said surface (2) so as to increase the temperature of the surface, upon receiving the decreased moisture content signal from the detector means (9).

22. An apparatus according to claim 15 further including a second moisture sensor (13, 42) for monitoring moisture content of gas (A) upstream of said surface (2).

23. An apparatus according to claim 22 wherein said second moisture sensor (13, 42) is pre-calibrated to obtain direct readings of the dew point temperature ($T_D$) of a moist gas (A).

24. An apparatus according to claim 19 further comprising a second moisture sensor for monitoring moisture content of gas upstream of said surface, and wherein the signal processing means (20, 60) is programmed to compare a direct dew point reading obtained from said second sensor (13, 42) with the calculated average value of the temperature (T) of said surface (2) during the dew point temperature measuring period and to re-calibrate the pre-calibrated second moisture sensor if the compared direct reading and calculated average value do not match.

25. An apparatus according to claim 15 wherein the moisture sensor (5, 13, 42, 44) is of a type having an electrical capacitance which varies with changes in moisture content of the atmosphere to which the sensor is exposed.

26. An apparatus according to claim 15 wherein said cooling system comprises a thermoelectric heat pump (3, 56) incorporating Peltier crystals.

27. An apparatus according to claim 26 wherein said surface (2) comprises a layer of heat-conducting material in contact with said heat pump (3).

28. An apparatus according to claim 15 wherein said surface comprises an inner surface of part of a wall of a tube (40) through which a flow of moist gas (A) is passed.

29. An apparatus according to claim 28 wherein said cooling system comprises a reservoir of thermally conductive liquid (51) in which a portion of said tube (40) is submerged, the temperature of the liquid refrigerant being controlled by thermoelectric temperature control means (56).

30. An apparatus according to claim 28 wherein said cooling system comprises a chamber (70) having a restricted orifice (72) through which compressed gas is supplied to the chamber, a portion of said tube (40) being located in said chamber, whereby expansion of the compressed gas into the chamber (70) results in cooling of said portion of the tube.

31. An apparatus according to claim 30 wherein said apparatus is portable.

32. An apparatus according to claim 19 further including additional temperature measuring means (92), readings from which are utilized by the signal processing means (20, 60) to express dew point temperature readings obtained from the apparatus in terms of relative humidity.

33. An apparatus according to claim 19 further comprising a second moisture sensor for monitoring moisture content of gas upstream of said surface, and wherein the signal processing means (20, 60) is programmed to pre-calibrate at least one of the moisture sensors (5, 13, 42, 44) to give instantaneous dew point temperature values for measured moisture content readings.

34. An apparatus according to claim 33 wherein the signal processing means (20, 60) is programmed to pre-calibrate both the moisture sensors (5, 13, 42, 44), to identify any failure of either one of the moisture sensors, and to subsequently display dew point temperature readings obtained from the remaining functional one of the pre-calibrated moisture sensors.

35. An apparatus according to claim 19 further comprising a second moisture sensor for monitoring moisture content of gas upstream of said surface, said second moisture sensor being pre-calibrated to obtain direct readings of the dew point temperature of a moist gas, and wherein the signal processing means (20, 60) is programmed so that, upon any failure of the temperature measuring means (7, 62) or the cooling system (3, 51, 56), the apparatus continues to operate by displaying dew point readings obtained from the pre-calibrated second moisture sensor (13, 42).

36. An apparatus according to claim 19 wherein the signal processing means (20, 60) is programmed to estimate the useful working life of the moisture sensor based on readings taken therefrom during operation of the apparatus.

* * * * *